(12) United States Patent
Srocka

(10) Patent No.: US 9,587,930 B2
(45) Date of Patent: Mar. 7, 2017

(54) METHOD AND ASSEMBLY FOR DETERMINING THE THICKNESS OF A LAYER IN A SAMPLE STACK

(71) Applicant: HSEB Dresden GmbH, Dresden (DE)

(72) Inventor: Bernd Srocka, Berlin (DE)

(73) Assignee: HSEB Dresden GmbH, Dresden (DE)

( * ) Notice: Subject to any disclaimer, the term of this patent is extended or adjusted under 35 U.S.C. 154(b) by 0 days.

(21) Appl. No.: 15/223,424

(22) Filed: Jul. 29, 2016

(65) Prior Publication Data

US 2017/0030707 A1 Feb. 2, 2017

(30) Foreign Application Priority Data

Jul. 30, 2015 (EP) ..................................... 15178999

(51) Int. Cl.
*G01B 11/28* (2006.01)
*G01B 11/06* (2006.01)

(52) U.S. Cl.
CPC ................................ *G01B 11/0616* (2013.01)

(58) Field of Classification Search
CPC ............................ G01B 11/28; G01B 11/0616
(Continued)

(56) References Cited

U.S. PATENT DOCUMENTS 5,091,647 A 2/1992 Carduner et al.
5,486,701 A 1/1996 Norton et al.
(Continued)

FOREIGN PATENT DOCUMENTS

EP 0 545 738 A2 12/1992
EP 2 426 717 3/2012
(Continued)

*Primary Examiner* — Roy M Punnoose
(74) *Attorney, Agent, or Firm* — Thorpe North & Western LLP

(57) ABSTRACT

A method for determining the thickness of a layer in a sample stack of at least two layers with an assembly comprising a light source for illuminating a stack of layers and a detector for detecting light reflected by the stack of layers in a defined first wavelength range, the method comprises a first step of obtaining a calibration curve by the calibrating steps of providing two or more reference stacks of layers, where each layer of the reference stacks has a known thickness, the same material as the sample stack and the layers occur in the same order as in the sample stack; illuminating the reference stacks with light from the light source; and detecting the intensity of light reflected by the reference stacks with the detector in the first wavelength range. Further steps of the method comprise illuminating the sample stack of layers with light from the light source; detecting the intensity of the light reflected by the sample stack of layers with the detector in the first wavelength range; and determining the thickness of the layer comprised in the sample stack of layers from the intensity detected by the detector by means of the calibration curve. The method is characterized in that further calibration curves are obtained of reference stacks, where the thickness of another, different layer is known also, thereby providing a first series of calibration curves in the first wavelength range; a second plurality of calibration curves is obtained in the same way as the first series of calibration curves for a further wavelength range; and the thickness of the layer of the sample stack is determined from the intensity detected by the detector by means of the first and second series of calibration curves.

13 Claims, 10 Drawing Sheets

(58) Field of Classification Search
USPC .......................................................... 356/630
See application file for complete search history.

(56) References Cited

U.S. PATENT DOCUMENTS

| | | | |
|---|---|---|---|
| 7,151,609 B2 * | 12/2006 | Chalmers | G01B 11/0625 |
| | | | 356/326 |
| 2013/0063733 A1 | 3/2013 | Kuwabara | |
| 2014/0293295 A1 | 10/2014 | Kuwabara | |

FOREIGN PATENT DOCUMENTS

| | | |
|---|---|---|
| WO | WO 00 26614 A1 | 5/2000 |
| WO | WO 2014/072109 A1 | 5/2014 |

* cited by examiner

METHOD AND ASSEMBLY FOR DETERMINING THE THICKNESS OF A LAYER IN A SAMPLE STACK

TECHNICAL FIELD

The invention relates to a method for determining the thickness of a layer in a sample stack of at least two layers with an assembly comprising a light source for illuminating a stack of layers and a detector for detecting light reflected by the stack of layers in a defined first wavelength range, the method comprising the steps of
(a) obtaining a calibration curve by the calibrating steps of
  (A) providing two or more reference stacks of layers, where each layer of the reference stacks has a known thickness, the same material as the sample stack and the layers occur in the same order as in the sample stack;
  (B) illuminating the reference stacks with light from the light source; and
  (C) detecting the intensity of light reflected by the reference stacks with the detector in the first wavelength range;
(b) illuminating the sample stack of layers with light from the light source;
(c) detecting the intensity of the light reflected by the sample stack of layers with the detector in the first wavelength range; and
(d) determining the thickness of the layer in the sample stack of layers from the intensity detected by the detector by means of the calibration curve.

The invention further relates to an assembly for determining the thickness of a layer in a sample stack of at least two layers comprising
(a) a light source for illuminating a stack of layers;
(b) a detector for detecting light reflected by the stack of layers in a defined first wavelength range, and
(c) two or more reference stacks of layers, where each layer of the reference stacks has a known thickness, the same material as the sample stack and the layers occur in the same order as in the sample stack.

In different branches of the industry flat products are inspected with optical methods regarding their properties. In the semiconductor and solar cell industry these flat products are, amongst others, wafers. Wafers are discs of semiconductor, glass, sheet, or ceramic materials. Such inspected properties may be the layer thickness of single and double layer stacks on the surface of the objects. Layers of different materials are used, for instance, within the production of electronic semiconductor devices ("chips").

A particular field of interest is the fabrication of special wafers, so called SOI (Silicon-on-Insulator) wafers, for modern semiconductor devices. These wafers have a double layer on the top surface. Such a double layer or layer stack is composed of a silicon oxide layer and a silicon layer on top of it. In a modern approach regarding new devices especially with lower power and/or high performance the two layers have a thickness in the range of several nanometers. The very small layer thicknesses strongly influence the performance of the chips produced on the wafers. Their accuracy and lateral homogeneity are, therefore, very important for the chip manufacturing process and the later device performance. It is, hence, of particular interest to measure the thickness and its homogeneity during the manufacturing process with high lateral resolution, high accuracy and within in a short time per wafer.

Similar requirements must be fulfilled in other fields. The thickness and lateral homogeneity of double layer stacks may be of crucial importance for end product parameters.

PRIOR ART

Ellipsometric measurements for nondestructive layer analysis are known in the art. A sample is illuminated with polarized light. The light is reflected at the interfaces between the layers or transmitted and finally detected. The properties of the layers are determined by the change of the polarization state of the detected light. Such measured values depend very much on the focus position and the inclination of the surface of the sample. On the other hand, this method is highly accurate if an appropriate layer model is used. Such a method is, however, time consuming requiring several tens of seconds per point and its spatial resolution is restricted to a few tens of µm.

Patent publications WO2014072109, EP2426717, US2014293295, and US2013063733 disclose the determination of the thickness of one layer (film) of a double layer stack only using the measurement of the intensity of the reflected light. The disclosed methods are useful for a measurement where the nominal thickness of both layers is known and only small deviations from such nominal thickness values are to be determined. The key idea in all three publications is to restrict the measurement to a small wavelength range selected in such a way that the influence of the second layer is minimal. The deviation of the intensity of the reflected light versus thickness variation is nearly zero within the selected small wavelength range. This idea is based on the fact that the intensity of the light reflected by a two layer stack on top of a substrate varies strongly with the wavelength range due to the interference of the optical waves in dependence of the thicknesses of the layers. The described methods differ in terms of how to get a good reference for the calibration of the method and which is the best way to avoid influences from the second layer. The methods can be used either for the top or the bottom layer within the inspected double layer stack selecting different appropriate small wavelength ranges. However, all methods mentioned above assume that the influence of the second layer thickness variation is neglectable within the selected wavelength range. In reality however, it may not be neglected and for a high resolution method the influence of the second layer can be as high as several percent, rendering the measured result to be useless.

The general physics of the wave reflection at interfaces between two materials are described by Fresnel formulas. According to the formulas the dependency of the travelling speed of electromagnetic waves inside a material on the material parameters are well known in the art. Material parameters are, for example, the refraction index, the effect of the linear interference of waves, and the usage of the three basics to determine the layer thicknesses of single and stacked layers. The refraction index can be a complex value describing the refraction and the absorption. The method is summarized, for instance, in WO2014072109. It is the basic idea of the prior art inspection methods to use the light reflected by a sample stack within small wavelength ranges where the influence of the second layer is minimal.

The influence of the two layers within a small thickness range can be described by approximated relations. A simple example uses a layer stack of two layers named, for example, A and B. Each of the layers of the two layer stack has a nominal thickness. A Taylor series at the point of the nominal layer thicknesses of layer A and B can be used to calculate the reflected light intensity R:

$$R = R_0 + \frac{\partial tR}{\partial t_A}\Delta t_A + \frac{\partial tR}{\partial t_B} + \Delta t_B + \qquad(1)$$
$$\frac{\partial^2 tR}{\partial t_A^2}(\Delta t_A)^2 + \frac{\partial^2 tR}{\partial t_B^2}(\Delta t_B)^2 + \frac{\partial^2 tR}{\partial t_A \partial t_B}\Delta t_A \Delta t_B + \cdots$$

wherein
- $t_A$: thickness of layer A
- $t_B$: thickness of layer B
- $t_{A0}$: nominal thickness of layer A
- $t_{B0}$: nominal thickness of layer B
- $R_0$: actual reflected light intensity measured at the point where layers A and B have the thickness values $t_A$ and $t_B$.
- $R_0$: reflected light intensity where each layer has the nominal thickness, i.e. $t_A = t_{A0}$ and $t_B = t_{B0}$ $$\frac{\partial x}{\partial y} \text{ and } \frac{\partial^2 x}{\partial y^2}$$

denote partial derivatives of first or second order, respectively, taken at
the point where the layers A and B have their nominal thickness values
$\Delta t_A$ denotes the difference $\Delta t_A = t_A - t_{A0}$;
$\Delta t_B$ denotes the difference $\Delta t_B = t_B - t_{B0}$.

The reflected light intensity R varies over the wavelength due to the interference of the optical waves in dependence of the thicknesses of the two layers. The selection of a wavelength range where the influence of one of the layers, for example layer B, is neglectable as it is necessary in prior art measurements means that a wavelength range must be found where $$\frac{\partial R}{\partial t_B}$$

is nearly zero while $$\frac{\partial R}{\partial t_A}$$

is not zero. Expressed more exactly $$\frac{\partial R}{\partial t_B}$$

must be much smaller than $$\frac{\partial R}{\partial t_A}.$$

If higher orders of derivatives are neglected, since their influence is usually smaller in a Taylor series, the equation (1) then reads:

$$R = R_0 + \frac{\partial R}{\partial t_A}\Delta t_A + \frac{\partial^2 R}{\partial t_A^2}(\Delta t_A)^2 \qquad(2)$$

Such a relation can be easily used to determine the layer thickness $t_A$ assuming that $t_B$ has its nominal value $t_B = t_{B0}$ and has, therefore, neglectable influence on R. The thickness of layer A can be determined by using a calibration method for the relation between R and $t_A$. For the calibration, layer stacks are manufactured with $t_B = t_{B0}$ and $t_A$ with several thickness values around $t_{A0}$. The layer stack samples are then measured by a reference method, e.g. ellipsometry, with high accuracy. A calibration curve $R = f(t_A)$, similar to the one shown in FIG. 5, can then be created from the measured intensity values at the measured points. This method is disclosed in above mentioned WO2014072109. The method has the disadvantage that layer B is assumed to be exactly at its nominal value $t_B = t_{B0}$ at all points. The influence of the thickness of layer B is entirely neglected. This neglection causes a systematic error of the determined thickness $t_A$ of layer A, which cannot be resolved within the known methods.

The same consideration holds vice versa for a determination of layer thickness $t_B$ under the assumption that $t_A$ has its nominal value $t_A = t_{A0}$.

DISCLOSURE OF THE INVENTION

It is an object of the invention to provide an assembly and a method of the above mentioned kind which allows an accurate measurement of the thickness of one or more layers simultaneously with high accuracy, high speed, and in the single micron and sub-micron lateral resolution range.

According to an aspect of the invention this object is achieved with the method of the above mentioned kind, which is characterized in that:
(e) further calibration curves are obtained of reference stacks, where the thickness of another, different layer is known also, thereby providing a first series of calibration curves in the first wavelength range;
(f) a second plurality of calibration curves is obtained in the same way as the first series of calibration curves for a further wavelength range;
(g) the thickness of the layer of the sample stack is determined from the intensity detected by the detector by means of the first and second series of calibration curves.

With such a method it is possible not only to determine the thickness of one layer in a two-layer stack more accurately, but also to determine the thickness of two or even more layers. The measurement in two different wavelength ranges requires the use of two series of calibrating curves. One series for each wavelength range. Each series provides information about the intensity of the reflected light under known thickness conditions. If two or more thicknesses are to be determined, the combination of the thicknesses of the different layers of a stack belonging to one specific reflectivity is not unambiguous. It is an important feature of the invention that such combination can be found by using different wavelength ranges. The term wavelength range means the range which can be represented by one single wavelength value, i.e. the range transmitted by an interference filter or the like and is not meant to extend far beyond several tens of nanometers.

Preferably, the intensity of the light reflected by a stack of layers is detected simultaneously for two wavelength ranges. Thereby, the measurements can be carried out faster and variations of the set-up will not have any influence. Also, it can be useful to use normalized values by subtracting dark values and normalizing the measured intensities by a reference value which has, for example, not been reflected at the stack of layers.

In a preferred modification of the invention the wavelength ranges are selected such that in each wavelength range the influence of a thickness change of one layer on the intensity of the light reflected by the stack of layers is much larger than the influence of a thickness change of the other layers. While this is not necessary for the invention it may be advantageous because the terms in the Taylor series decrease faster.

Alternatively, the wavelength ranges are selected such that the overall intensity of the reflected light is optimized. This will enable a good signal-to-noise ratio and provide good accuracy.

In a further modification of the invention the intensity of the reflected light is measured at more than two wavelength ranges. This enables either a higher accuracy by redundant measurements or the determination of the thickness of further layers.

The thickness of three or more layers of the stack may be determined by calibrating and detecting the intensity of the reflected light in three or more wavelength ranges.

Preferably, the thickness of the layers of the reference stacks are determined by ellipsometry for calibration. While ellipsometry is very accurate and provides good reference values it is too slow to be used in routine measurements. The use of ellipsometry for the measurement of the thicknesses of the reference stacks is, however, a good way to obtain excellent calibration curves.

The invention can be carried out with an assembly for determining the thickness of a layer in a sample stack of at least two layers of the above mentioned kind. The assembly according to the invention is characterized in that
(e) further reference stacks are provided, where the thickness of another, different layer is known for providing a first series of calibration curves in the first wavelength range;
(f) means for detecting light reflected by the stack of layers in a defined second wavelength range for providing a second series of calibration curves for a further wavelength range.

The means for detecting light in a defined second wavelength range can be a detector with a wavelength selecting means, such as a filter, a monochromator or the like if a broad band light source is used and a detector without any wavelength selecting means if a more or less "monochromatic" light source is used. Such a light source must be either adjustable regarding the wavelength or at least two light sources with different wavelengths are used.

In a modification of the invention the light source is a light source with a continuous spectrum and one or more filters, an adjustable monochromator or another wavelength selection means is provided to define the measured wavelength range.

Alternatively, one or more light sources are provided which emit light in the defined wavelength ranges.

In practice it has been found that the different wavelength ranges may well be defined by two interference filters or a couple of interference filter pairs arranged in two filter wheels. The different wavelength ranges may also be defined by a single or a combination of acusto-optical filters.

Preferably, the detector is a line camera or an area camera. This enables the measurement of the intensity of the reflected light at a plurality of points and consequently the measurement of the thickness in several points.

It is a condition for the invention, that within two different wavelength ranges represented here by center wavelengths $\lambda_A$ and $\lambda_B$, the wavelengths are selected such that:
$$\lambda_A \neq \lambda_B$$
both layer thicknesses $t_A$ and $t_B$ influence the intensity of the reflected light at at least one of the two wavelengths $\lambda_A$ and $\lambda_B$ and
the intensity of the reflected light at both wavelengths $\lambda_A$ and $\lambda_B$ is influenced by at least one of the two layer thicknesses $t_A$ and $t_B$
whereby two thickness values $t_A$ and $t_B$ of the two layers A and B of the stack from the two measured intensities of the light reflected within the two selected wavelength ranges around $\lambda_A$ and $\lambda_B$ can be determined.

According to the present invention the thickness of both layers is taken into account. Thereby, the error produced by measurements of the prior art by neglecting the influence of the second layer is minimized. According to the invention the reflected intensities at two wavelength ranges are measured and both results are combined. The two wavelength ranges are represented here by their center wavelengths $\lambda_A$ and $\lambda_B$. They are selected such that at $\lambda_A$ the influence of layer B is minimal, i.e.

$$\frac{\partial R}{\partial t_B} \approx 0,$$

and at $\lambda_B$ the influence of layer A is minimal, i.e $$\frac{\partial R}{\partial t_A} \approx 0.$$

The calibration procedure is similar as the one described in the prior art. According to the present invention, however, thicknesses of both layers are varied around their nominal values. As with known methods, the stacks of the two layers are measured with a reference method, e.g. ellipsometry. The intensities of the reflected light are measured in two wavelength ranges around their center wavelengths $\lambda_A$ and $\lambda_B$. Such wavelength ranges may be small. Thereby, two intensity values $R_A$ and $R_B$ derived from the reflection measurements at $\lambda_A$ and $\lambda_B$ respectively, are obtained for each point to be measured having the thickness value pair $[t_A, t_B]$. Sorting all values, two fields of calibration functions $R_A$ and $R_B$ can be established having the form $R=f(t_A,t_B)$, one for each reflected light intensity:

$$R_A = f(t_A, t_B) \text{ measured at } \lambda_A \text{ where } \frac{\partial R}{\partial t_A} \approx 0 \qquad (4)$$

$$R_B = g(t_A, t_B) \text{ measured at } \lambda_B \text{ where } \frac{\partial R}{\partial t_A} \approx 0 \qquad (4)$$

where f and g denote the functional relations of R from the thickness values.

The layer thicknesses at point X of an unknown sample can be inspected by measuring two intensity values $R_{AX}$ and $R_{BX}$ at point X. From the series of calibration curves described by formulas (3) and (4) specific relations between $t_A$ and $t_B$ can be derived for the measured values $R_{AX}$ and $R_{BX}$. Measured values $R_{AX}$ and $R_{BX}$ are taken as fixed input parameters. Assuming simple linear correlations between $t_A$ and $t_B$ around the nominal point $[t_{A0}, t_{B0}]$ the following equations are obtained:

$$t_A = [f(t_A, t_B)]_{R_{AX}} = t_{A_0} + \left[\frac{\partial t_A}{\partial t_B}\right]_{t_B = t_{B0}} t_B \text{ measured at } \lambda_A \quad (5)$$

$$t_B = [g(t_A, t_B)]_{R_{BX}} = t_{B_0} + \left[\frac{\partial t_B}{\partial t_A}\right]_{t_A = t_{A0}} t_A \text{ measured at } \lambda_B \quad (6)$$

These two equations can be combined in a simple manner. Replacing $$\left[\frac{\partial t_A}{\partial t_B}\right]_{t_B = t_{B0}}$$

by $$\left[\frac{\partial t_A}{\partial t_B}\right]_{B0} \text{ and } \left[\frac{\partial t_B}{\partial t_A}\right]_{t_A = t_{A0}} \text{ by} \left[\frac{\partial t_B}{\partial t_A}\right]_{A0}$$

and using equation (6) to solve (5) provides:

$$t_A = t_{A_0} + \left[\frac{\partial t_A}{\partial t_B}\right]_{B0} t_B = \quad (7)$$

$$t_{A_0} + \left[\frac{\partial t_A}{\partial t_B}\right]_{B0}\left(t_{B_0} + \left[\frac{\partial t_B}{\partial t_A}\right]_{A0} t_A\right) = \frac{t_{A_0} + \left[\frac{\partial t_A}{\partial t_B}\right]_{B0} t_{B_0}}{1 - \left[\frac{\partial t_A}{\partial t_B}\right]_{B0}\left[\frac{\partial t_B}{\partial t_A}\right]_{A0}}$$

Thus, using (7) and (6) both thickness values $t_A$ and $t_B$ can be determined without the systematic error caused by neglecting the combined influence of both layers on the reflectivity.

Obviously, the linear approach is used here only to demonstrate the method in a simple manner. In a more sophisticated approach better approximations than linear ones can be used instead of the relations (5) and (6). Such more sophisticated approaches include, for example, a polynomial of second, third or even higher order which are fitted, for example, by the method of least squares. Thereby, the best fitting values for $t_A$ and $t_B$ can be determined.

The method according to the present invention is not restricted to the selection of wavelength ranges for the measurement with the condition described in (3) and (4). The method is not necessarily such that at $\lambda_A$ the influence of the layer B is small, i.e.

$$\frac{\partial R}{\partial t_B} \approx 0,$$

and at $\lambda_B$ the influence of the layer A is small, i.e.

$$\frac{\partial R}{\partial t_A} \approx 0.$$

The only conditions for the two wavelength ranges at wavelengths $\lambda_A$ and $\lambda_B$ are the ones mentioned above.

It is hence possible to select the wavelengths $\lambda_A$ and $\lambda_B$ by other criteria, as, e.g., a sufficient overall reflected intensity or the usability for different layer materials and/or thickness compositions. This greater freedom in the selection of $\lambda_A$ and $\lambda_B$ allows to improve the stability of the method. This can be achieved, for example, by using wavelength ranges with good overall reflection to increase the detected signal. Alternatively, it is possible to measure different materials and/or thickness compositions with the same assembly and even with the same filters or other wavelength selection means.

An assembly according to the present invention also comprises calculation means to process the measured intensities and calculate from the two values the two thickness values of the two layers of the stack. While it is possible to measure and or process the values simultaneously, obviously this can be carried out in series also.

Further modifications of the invention are subject matter of the subclaims. An embodiment is described below in greater detail with reference to the accompanying drawings.

DESCRIPTION OF THE EMBODIMENTS

Figure 9:
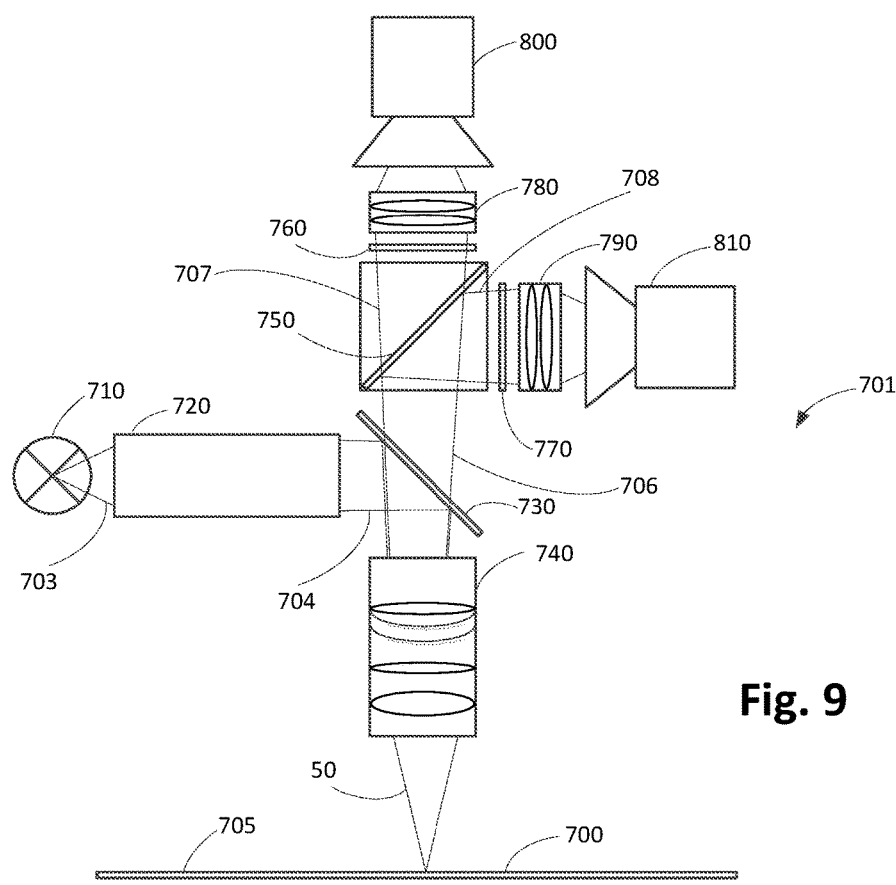
FIG. 9 is a schematical illustration of a device for measuring reflectivity at different wavelengths simultaneously with two detectors each having its own optics.

FIG. 9 shows an assembly 701 to measure reflectivity of a sample designated with numeral 700 at different wavelength ranges. The sample 700 has a layer stack 702, shown in detail in FIG. 1, to be inspected. Broadband light 703 from a light source 710, such as an LED, a tungsten lamp or an arc discharge lamp, is homogenized by optical means 720. The optical means homogenize the lateral light distribution. This can be achieved by, for example a glass rod with hexagonal cross section or a diffusor. The homogenized light is then deflected by a 50% mirror 730 through an objective 740 onto the sample 700. This is represented by the schematically illustrated path of light designated with numeral 704.

The light is partially reflected from the surface 705 of the sample 700. The intensity of the reflected light 706 is modulated. The modulation is caused by the interference effect of light partially reflected at each of the material interfaces as described below. The light 706 which is reflected back passes the mirror 730 and is then split into two beams 707 and 708 by a beam splitter 750. In the present embodiment a 50/50 splitter is used. This, however, is not a condition for the method. In certain applications it might be useful to use other splitting ratios, e.g., to equalize the signal level in the case of very different intensity values of the reflected light within the used wavelength intervals. Filters 760 and 770 are provided in the light paths 707 and 708. The filters 760 and 770 define the wavelength intervals of the light to be used for the measurement. Obviously, alternative wavelength selection means, such as gratings, prisms and the like can also be used. The filters 760 and 770 let the desired small wavelength ranges pass and block all light having a different wavelength. Tube optics 780 and 790 are positioned behind the filter means and in front of sensor units 800 and 810, respectively. After each of the two measurement beams 707 and 708 passes its tube optics 780 or 790, respectively, the reflected light intensity is determined by detectors in the form of sensor assemblies 800 and 810 with detector arrays and signal processing means (not shown).

Since using the assembly 701 and a method described below require only intensity values to be measured, the sensor assemblies 800 and 810 can be a single element sensor, such as a photomultiplier or a photodiode or a multi-element sensor like e.g. a line camera or an area camera system, such as a CCD or CMOS detector. Using a multi-element sensor assembly allows to measure the spatial distribution and homogeneity of the layer thicknesses of the two layers very fast. The calculation described below in greater detail can be performed for each sensor pixel of the sensor assemblies separately. One measurement step thereby provides a large number of thickness values of an area or a line of the sample. By adding a movable station to the assembly 701, which provides a relative lateral movement between each of the sensor assemblies and the sample 700 it is possible to scan the whole sample surface 705 and create a full map of the thickness values of the whole surface 705.

By using different objectives 740 with different magnification, like it is common practice within a microscope, the lateral resolution of the sensor assembly can be adapted to the needs of the measurement task. Hence, it is possible to measure the thicknesses of two layers very accurately and with a lateral resolution as low as a few hundred nanometers with a high speed.

The measurement of the intensity in a limited wavelength range can be achieved in several ways. Filters 760 and 770 can be used in the form of fixed wavelength interference filters providing the best stability for the selected wavelength interval. In the present embodiment those filters 760 and 770 are placed inside a filter wheel. The suitable filter may then be selected dynamically before starting the measurement. In an alternative embodiment wavelength range is defined by dichroitic mirror combinations instead of filters. In a yet further embodiment dynamically adjustable filters are used, such as, for example, acusto-optical filters which are also commercially available to make the set up even more flexible and allow to adapt the used wavelength range more easily to different measurement tasks. More complex embodiments, which are not shown here, use optical monochromators to achieve a very high accuracy in the wavelength selection with a very small wavelength interval. Different embodiments use a light source having a limited wavelength range, such as a laser whereby no additional filter is needed.

It is obvious that the embodiment shown in FIG. 9 is only an example, and may be modified, e.g., to improve the measurement procedure in terms of stability and reproducibility or to save costs. For instance, the embodiment shown in FIG. 10 may be used where instead of two tube optics 770 and 780 only one common tube optic 820 is used for the reflected beam. This saves costs and makes the measurements independent from the influence of the tube optics. The disadvantage is, however, that the change of the filter characteristics of filters 760 and 770 due to the unparallel beam must be considered. Furthermore, another sensor assembly 830 is added to monitor the impinging light intensity of light 801 in order to use these data for an improvement of the reproducibility.

Figure 10:
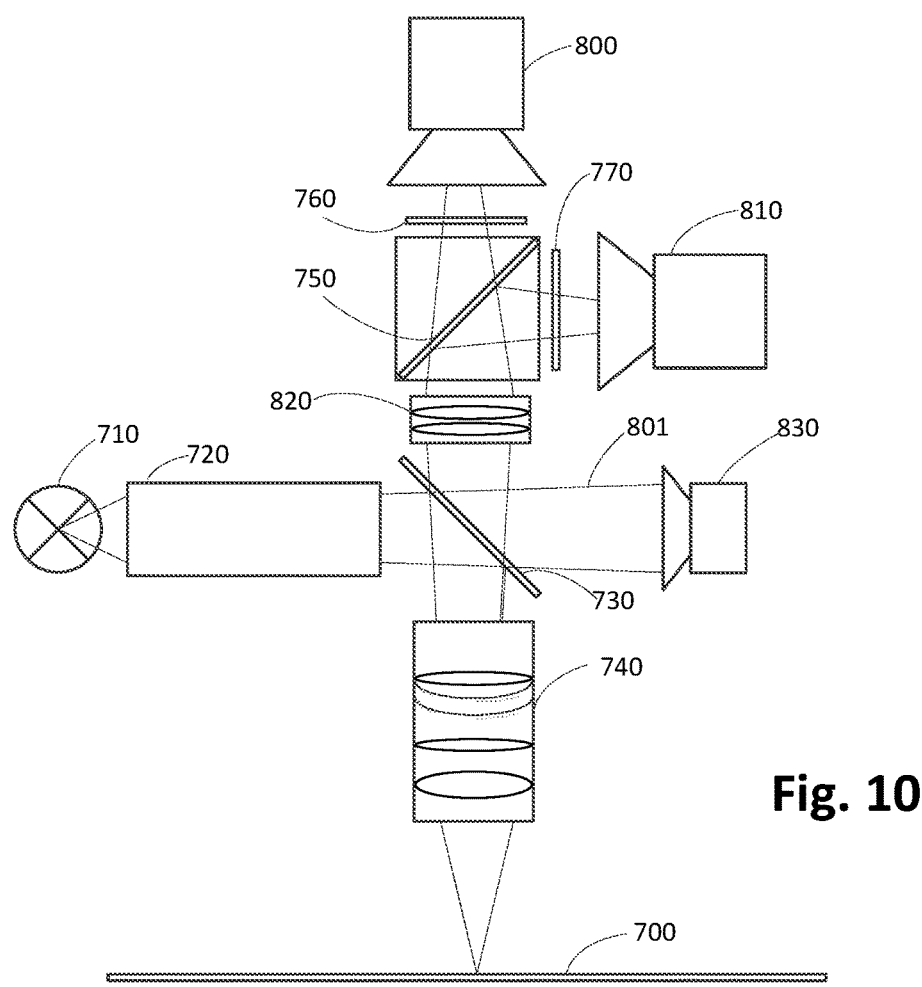
FIG. 10 is a schematic illustration of a device for measuring reflectivity at different wavelengths with two detectors using a common optics.

The assemblies 701 shown in FIGS. 9 and 10 enable the measurement of the reflection of the sample 700 at two different wavelength ranges with different center wavelengths.

Figure 1:
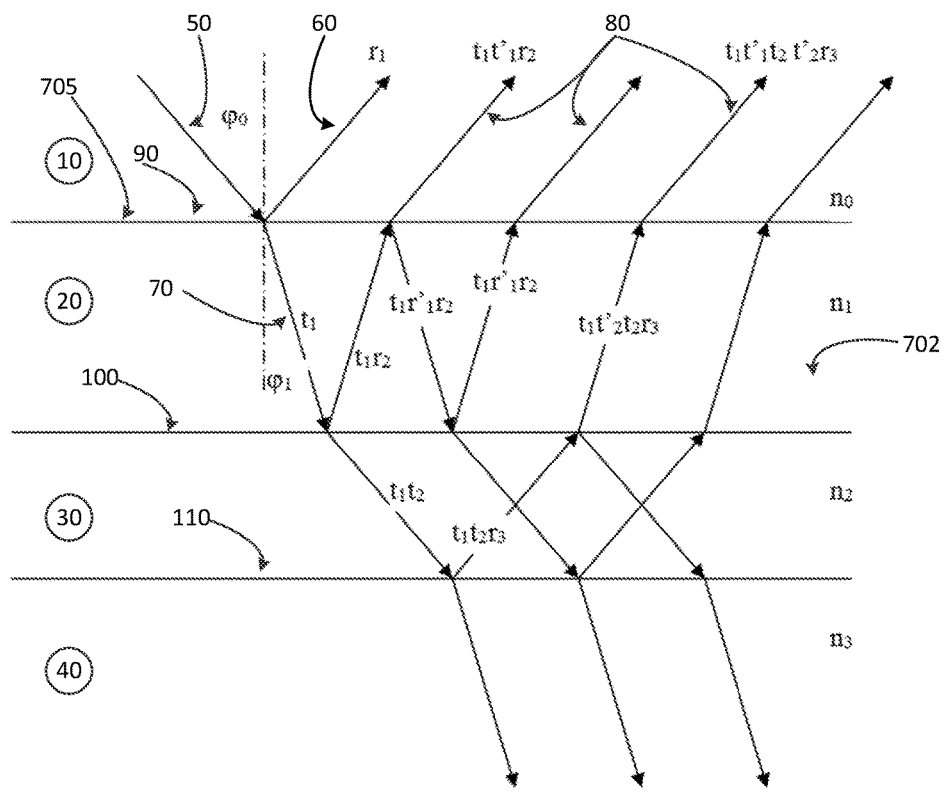
FIG. 1 schematically illustrates the reflection at double layer stack.

FIG. 1 illustrates the physical effects of the reflection at a sample 700. The sample 700 is a so-called double layer stack 702. The double layer stack 702 has a top layer 20 having a refraction index $n_1$ and a buried bottom layer 30 having a refraction index $n_2$. The layers 20 and 30 are stacked on a substrate material 40 having the refraction index $n_3$. While the substrate is part of the stack its thickness is not an issue regarding this invention. Therefore, the substrate does not constitute a "layer" as it is meant here. The stack 702 is placed in an environment of ambient material 10, which is air in the present embodiment. It may, however, be also vacuum, oil or water. The ambient material 10 has a refraction index $n_0$. As described above, light 50 is incident on the sample surface 705. The light 50 travels through the ambient material 10. The light is partially reflected at the interface 90 between the ambient material 10 and the top layer 20. Thereby, the light 50 is split into the initially reflected light 60 and light 70 transmitted through the interface 90 formed by surface 705 while it is refracted at the same time.

The light is also partially reflected and split into reflected and transmitted light at each further interface 100 and 110 between the materials 20 and 30, and 30 and 40, respectively.

All light incident on any of the interfaces 90, 100 or 110 between materials 10, 20, 30 or 40 with different refraction indices for multiple times will finally be reflected into ambient space 10. This is represented by the light beams 80. The intensity measured at sensor assemblies 800 and 810 of light beams 80 will be smaller intensities than the intensity of the incident light 50 due to the repeated reflection and transmission at the interfaces. Since the light 80 is composed of light travelling an additional way through the layer materials 20 and 30, the waves composing the light 80 are delayed in time with different time differences with respect to the initially reflected light 60. This causes an interference.

Thus, the intensity of the measured intensity including all reflected light 60 and 80 together is modulated by destructive and constructive interferences of light waves 60 and 80 according to their time delays. Since the time delays of light 80 are determined by the thickness of the layers 20 and 30 multiplied by their refraction index $n_1$ and $n_2$, respectively, the modulation of the intensity of the reflected light 80 is a function of the layer thicknesses of layers 20 and 30. Hence, analyzing the intensity modulation can be used to determine the layer thicknesses of the layers 20 and 30 using the refraction indices of the materials which are well known.

The formulas describing this effect are known as Fresnel equations together with the basic principle of the superposition of electromagnetic waves. The functions may also be determined by experiments, such as ellipsometry.

Figure 2:
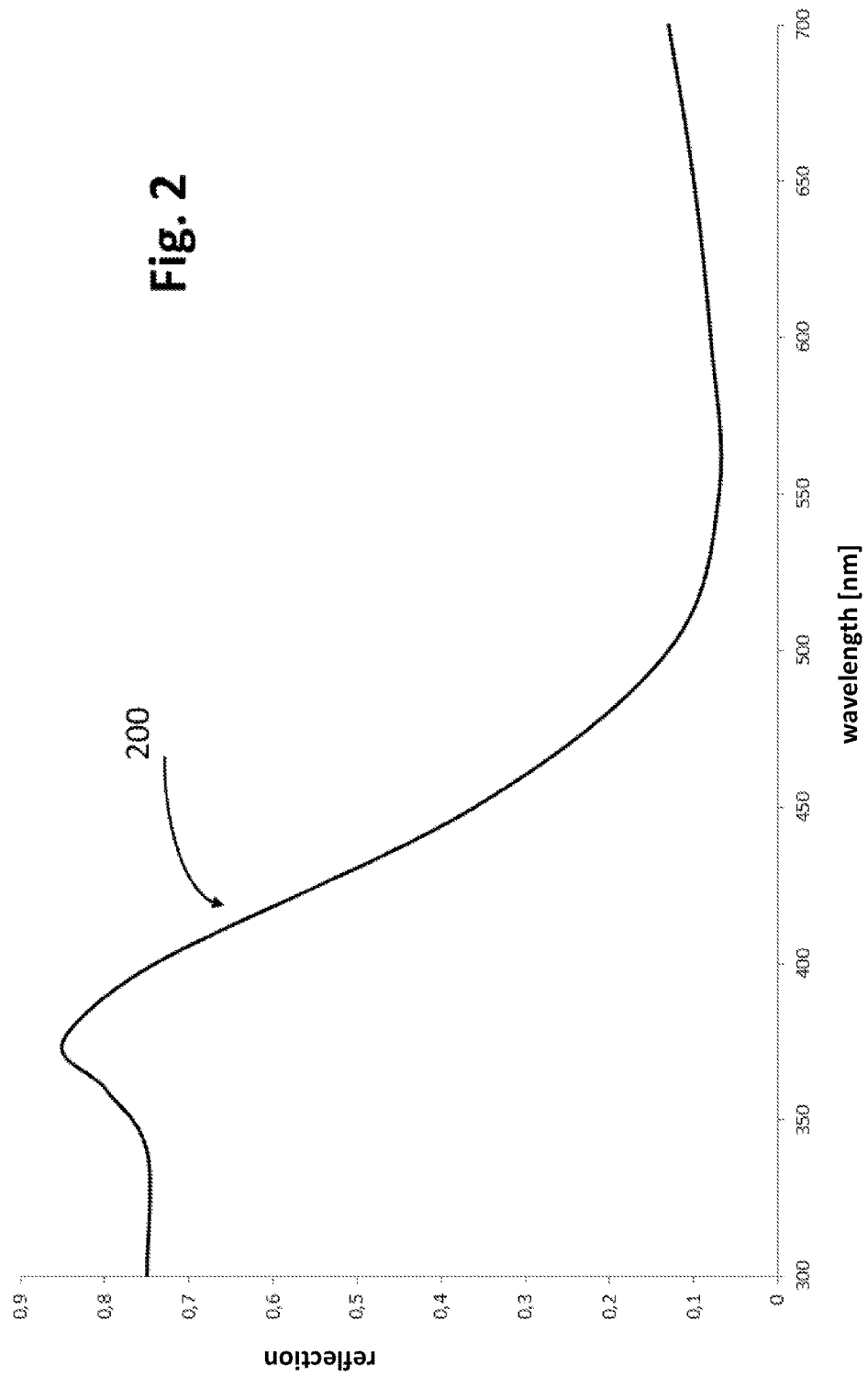
FIG. 2 shows a typical wavelength dependency of the reflection at multi-layer stack composed of a 12 nm silicon layer, a 25 nm silicon oxide layer and a silicon substrate.

If the intensity is determined as a function of the wavelength of the incident light 50 for a double layer stack with layers 20 and 30 of known material on a substrate 40 of known material within an environment of known ambient material 10, a reflection intensity function will be obtained. A typical reflection intensity function 200 is shown in FIG. 2 for a system with a top layer 20 in the form of a 12 nm Silicon layer and a buried layer 30 in the form of a 25 nm silicon oxide layer. The layers 20 and 30 are stacked on top of a substrate 40 of silicon within air as ambient material 10. FIG. 2 illustrates the effect by example and can be repeated for any material/thickness combination. The effective reflection coefficient for the whole ambient/layers/substrate system 200 is shown on the abszissa versus the wavelength in nm. It can be seen, that light in the range of 400 nm is reflected with a higher intensity than, for example, light in the range above 500 nm.

The measured intensity of the reflected light changes if the layer thickness of layer 20 or 30 changes. The change can be expressed mathematically in the form of the partial derivatives of the reflection divided by the layer thickness.

Figure 3:
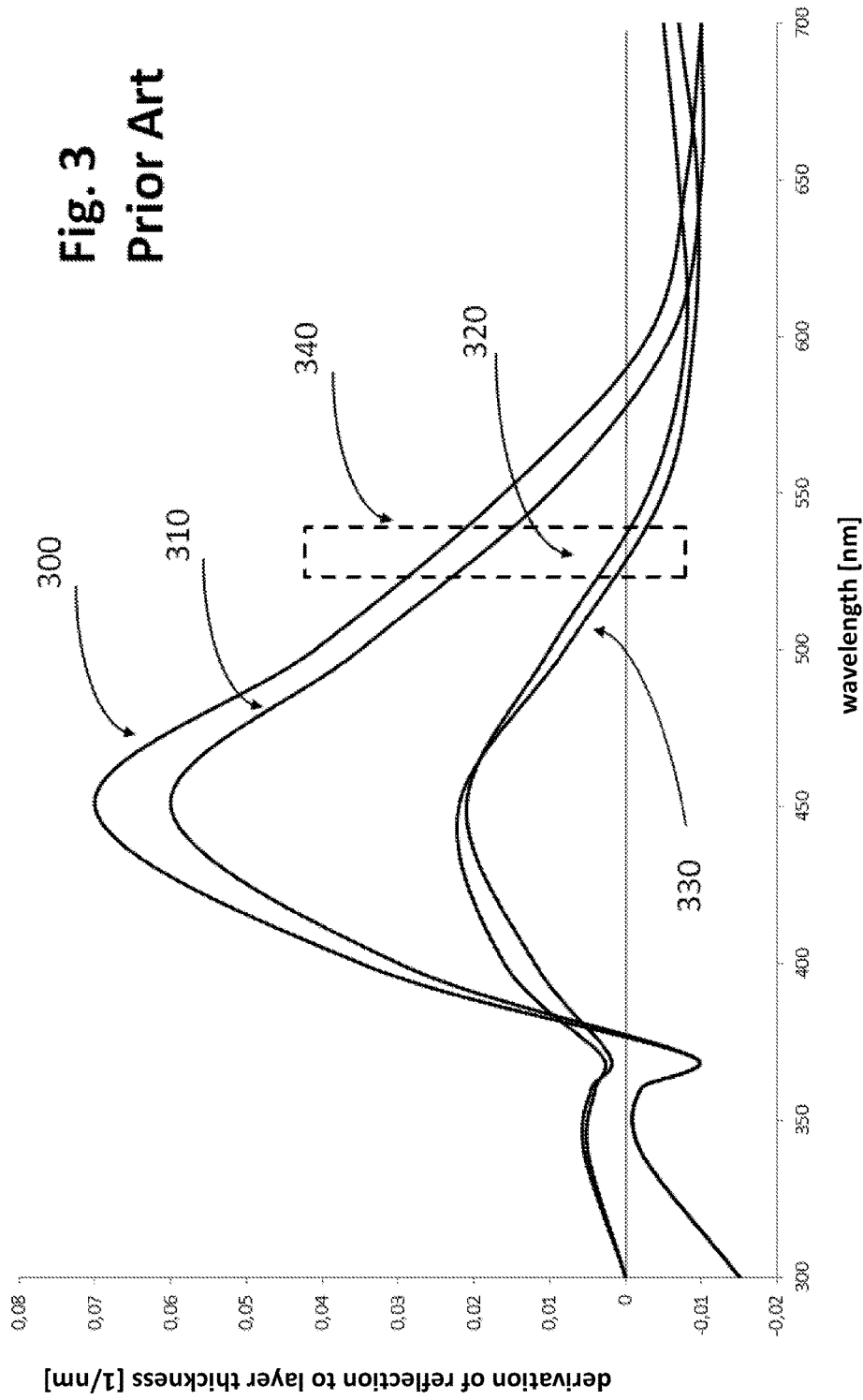
FIG. 3 (prior art) shows the wavelength dependency of the change of reflection at a multi-layer stack composed of a 12 nm silicon layer, a 25 nm silicon oxide layer and a silicon substrate due to changes in the thicknesses of the silicon and/or silicon oxide layer according to the single wavelength method.

FIG. 3 shows such ratio for the same wavelength range between 300 nm and 700 nm as FIG. 2. The curves 300 and 310 illustrate the influence of a change of the thickness of the silicon top layer 20. Curve 310 illustrates such influence with a slightly different thickness of the oxide layer 30. If curve 300 represents the nominal oxide thickness, curve 310 illustrates the effect of a variation in oxide thickness for the derivation of reflection to silicon top layer 20 thickness. In complex values this reads:

$$r = \frac{E_0^-}{E_0^+} = \frac{r_1 + r_2 e^{-2i\delta_1} + r_3 e^{-2i(\delta_1+\delta_2)} + r_1 r_2 r_3 e^{-2i\delta_2}}{1 + r_1 r_2 e^{-2i\delta_1} + r_1 r_3 e^{-2i(\delta_1+\delta_2)} + r_2 r_3 e^{-2i\delta_2}}$$

with $$\delta_l = \frac{2\pi}{\lambda} n_l d_l \cos \varphi_l$$

The square will then provide the reflectivity R.

In the same manner 320 and 330 show the influence of a change in the thickness of the buried oxide layer 30. Curve 330 represents a slightly different thickness of the silicon layer 20 compared to the nominal silicon thickness used for 320.

Figure 4:
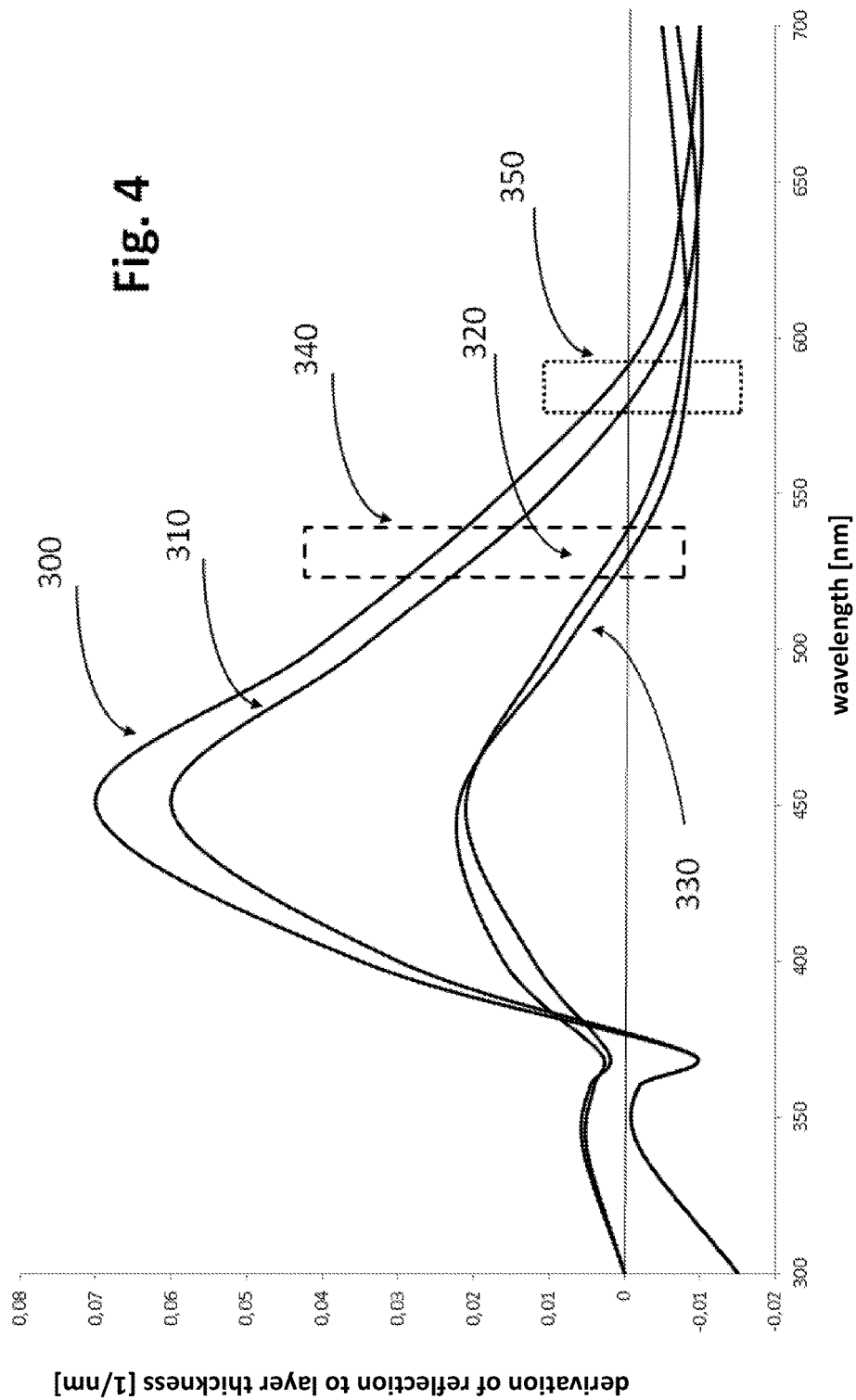
FIG. 4 shows the wavelength dependency of the change of reflection at a multi-layer stack composed of a 12 nm silicon layer, a 25 nm silicon oxide layer and a silicon substrate due to changes in the thicknesses of the silicon and/or silicon oxide layer with two wavelength intervals.

The dashed box 340 shows an appropriate wavelength range to measure the thickness of the silicon layer 20 with the single wavelength method known from the prior art. Known methods assume that due to the nearly zero value of the derivative of the reflection to oxide thickness as shown by 320 and 330, the influence from the thickness of the oxide be therefore ignored. However, since obviously curves 300 and 310 are not identical in the wavelength range 340 such neglection produces a systematic error. The present embodiment, therefore, uses a second small wavelength interval 350 for a second measurement, which is quasi independent from the first measurement in wavelength range 340 as shown in FIG. 4. Thereby, the two thickness layer values will be obtained by using the data from the two independent measurements of the reflection at two different wavelength intervals 340 and 350.

In order to obtain thickness values from reflectivity measurements a calibration is carried out. The prior art methods correlate the measured gray value to the "real" thickness values of the layers. Such "real" values are obtained by, for example, elipsometry. It is also possible to use straight forward calculations of the reflected light from the known material parameters for several thicknesses. In a real embodiment ellipsometry will, however, provide a good reference method.

Figure 5:
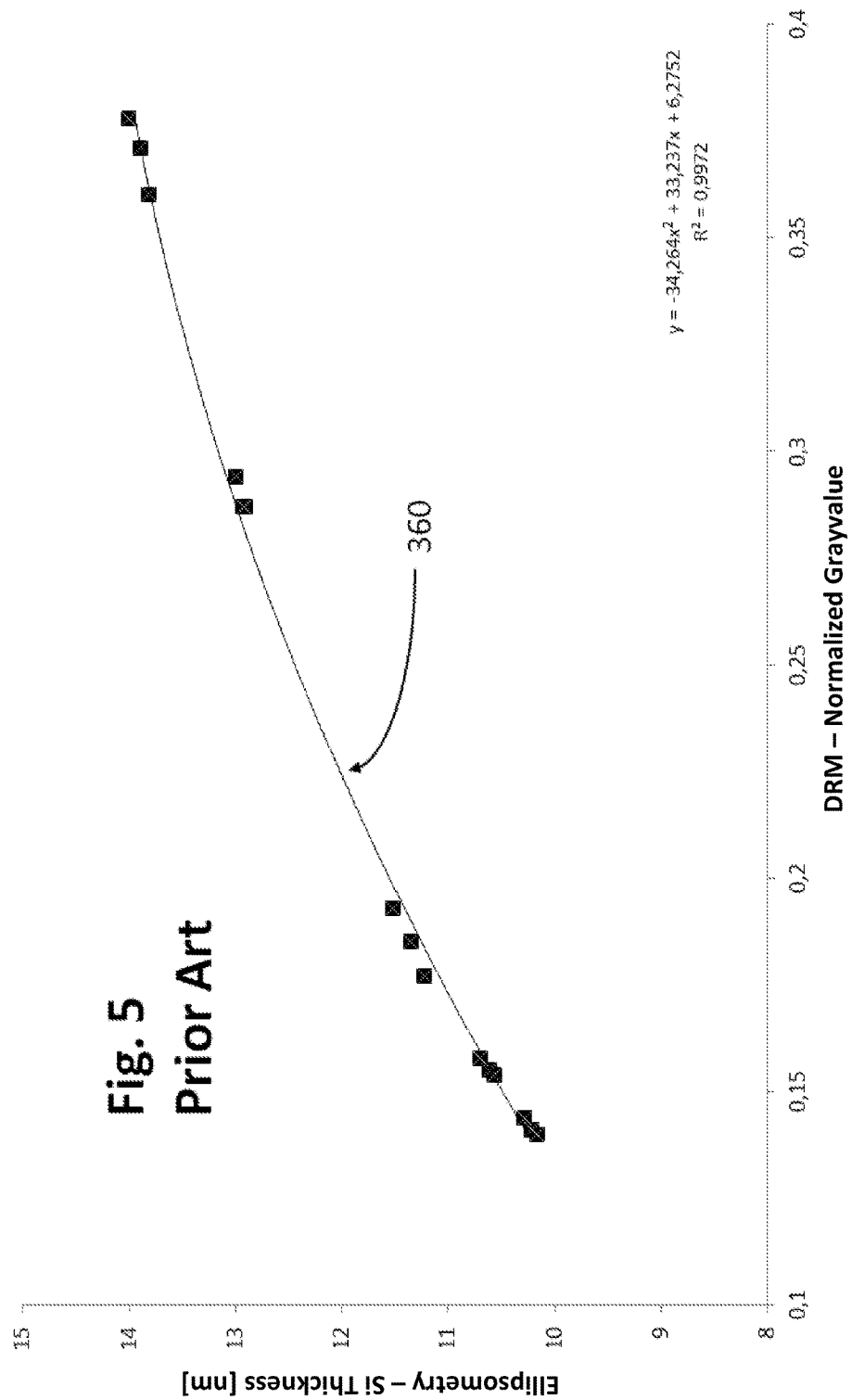
FIG. 5 (prior art) shows a calibration curve obtained with ellipsometry.

FIG. 5 shows a calibration curve 360 according to the prior art for a double layer system with a 25 nm thick buried bottom oxide layer and various samples having different silicon layer thicknesses. The reflectivity measurement is made under quasi monochromatic light conditions using only one small wavelength interval in the wavelength range 340 as illustrated in FIGS. 3 and 4. The reflected intensity is taken for this purpose as measured intensity normalized against some reflection standard, in order to exclude apparatus influences. The advantage of the approach using measured values and compare them with a reference method result is to avoid misinterpretations due to other effects like e.g. optical effects of the embodiment. The accuracy of the resulting calibration curve can be further enhanced by deriving the form of the curve from the theory by calculating the reflection intensity straight forward from known material parameters and thickness values measured by the reference method and searching for a best fit to the measured gray values.

Figure 6:
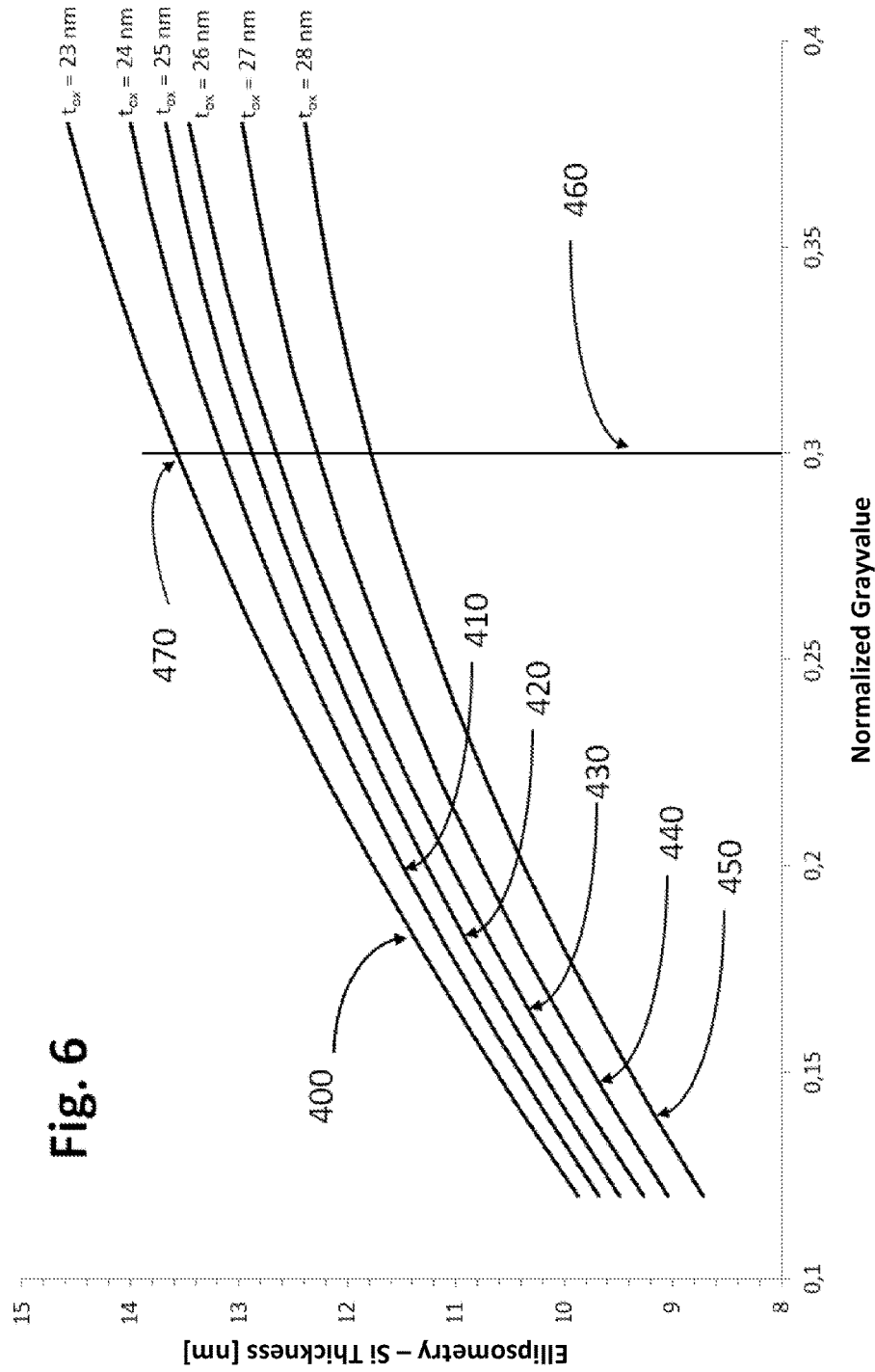
FIG. 6 shows a series of calibration curves for several samples with different oxide layer thicknesses.

The embodiment of the present invention calibrates by repeating the same procedure as used for the calibration curve 360 in FIG. 5 for a series of samples with different thicknesses of oxide layer 30. Thereby, a series of calibration curves 400, 410, 420, 430, 440, and 450 are obtained which are shown in FIG. 6. Calibration curve 400, for example represents the relation between different thicknesses of the silicon layer 30 and the measured intensity for a sample having a thickness of the oxide layer 30 of 23 nm. Calibration curve 410 shows the same with an oxide layer 30 having a thickness value of 24 nm. Samples with different thicknesses of the oxide layer 30 and with different thicknesses of the silicon layer 20 are measured. Again, all reflectivity measurements are carried out at first with light from one small wavelength interval within the range 340.

If ellipsometry is used as reference method for the determination of the silicon thickness, the oxide layer thickness is checked at the same time and the data value pairs sorted accordingly.

With such calibration curves, as shown in FIG. 6 unknown samples of the same material system but with unknown layer thicknesses can be inspected by measuring a specific reflectivity value. For example, if the normalized reflectivity gray level value is 0.3 as illustrated by the straight line 460 in FIG. 6, the crossing points of the measured reflectivity in the calibration curves 400, 410, 420, 430, 440, and 450 provide the relation between possible thickness values of the silicon layer 20 and the oxide layer 30. The point 470, for example, denotes a first possible combination of a thickness of the oxide layer 30 of 23 nm and a thickness of the silicon layer 20 of 13.6 nm (value on ordinate axis) fulfilling the measured reflectivity level at the line 460. This relation can be established for each calibration curve.

In other words: the measurement of the reflected intensity of an unknown sample at one wavelength will provide a plurality of possible thickness combinations which may be represented by a function. Such a function is represented in the form of curve 500 in FIG. 7. In order to select the correct values, the measurements are repeated in a second wavelength interval. In the present embodiment the interval in the wavelength range 350 (see FIG. 4) is used. The result is represented by curve 510 in FIG. 7.

Figure 7:
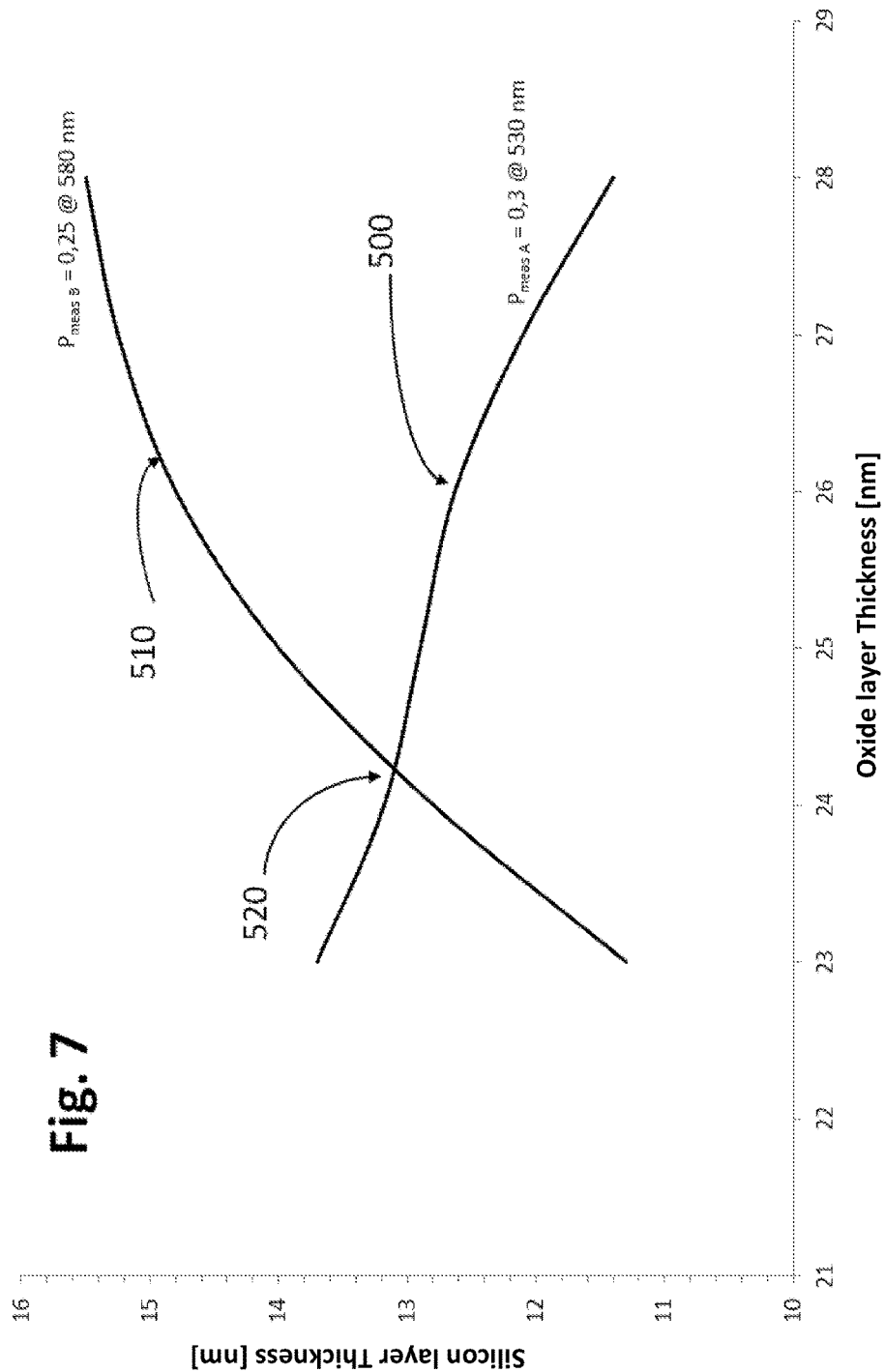
FIG. 7 illustrates the relation between possible thickness values of the top layer of silicon and the bottom layer of silicon oxide for two different wavelengths.

Two curves like curves 500 and 510 exist for any of those two measurements using different small wavelength intervals of impinging light. Any such pair of curves has just one crossing point 520 where the two measured reflection levels are obtained at the same time from the same two layer thickness values. In the example of FIG. 7 this results in a silicon layer thickness of 13.14 nm and an oxide layer thickness of 24.2 nm.

It is clear, that the given embodiment is only an example to illustrate the method according to the present invention. Similarly, the method can be used for any other material and/or thickness combination of a two layer stack on a substrate. Examples are among others strained silicon, silicon-germanium, germanium, gallium-arsenide, indium-phosphide, indium-arsenide, indium-gallium-arsenide, mercury-telluride, III-V and II-VI ternary and quaternary semiconductor alloys, other oxides and nitrides, photo resists, thin metal layers, glass, quartz and plastic materials.

Figure 8:
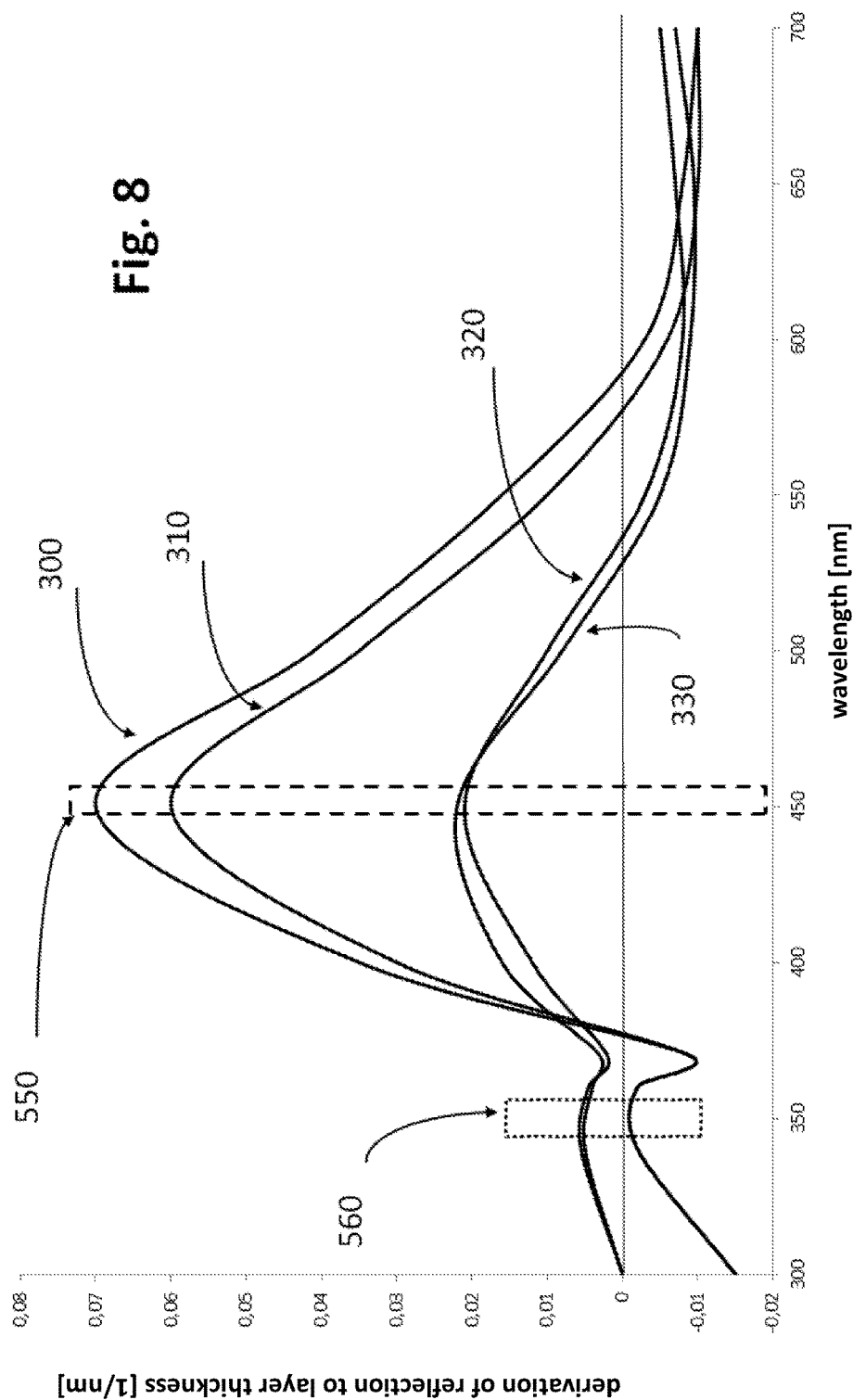
FIG. 8 is an alternative curve similar to FIG. 4, where the wavelength intervals are selected such that the resolution of the measurement is maximized.

From the above discussion it is also obvious, that the used wavelength intervals must not be selected such that the dependency of the reflection from one of the layer thickness values is minimized. They can be selected more freely e.g. to provide a high and approximately similar signal level for the reflection measurement to improve the measurement stability. This is illustrated in FIG. 8. The wavelength intervals 550 and 560 are used to maximize the resolution of the measurement.

Also it is of course possible to perform the two needed measurements sequentially while changing with the filters or the light source to select the wavelength interval between two consecutive measurements. Such a set up will not achieve the maximal possible overall measurement speed but may be less expensive. In such a set-up acusto-optical filters may be used to switch dynamical between the wavelength intervals very fast.

What is claimed is:

1. A method for determining the thickness of a layer in a sample stack of at least two layers with an assembly comprising a light source for illuminating a stack of layers with light and a detector for detecting light reflected by said sample stack of layers in a defined first wavelength range, the method comprising the steps of
    (a) obtaining a calibration curve by the calibrating steps of
        (A) providing two or more reference stacks of layers, where each layer of said two or more reference stacks has a known thickness, the same material as said sample stack and said layers of said two or more reference stacks occur in the same order as in said sample stack;
        (B) illuminating said reference stacks with light from said light source; and
        (C) detecting the intensity of said light reflected by said two or more reference stacks with said detector in said defined first wavelength range;
    (b) illuminating said sample stack of layers with light from said light source;
    (c) detecting the intensity of said light reflected by said sample stack of layers with said detector in said defined first wavelength range; and
    (d) determining the thickness of said layer in said sample stack of layers from the intensity detected by said detector by means of said calibration curve,
    and wherein
    (e) further calibration curves are obtained of reference stacks, where the thickness of another, different layer is known also, thereby providing a first series of calibration curves in said defined first wavelength range;
    (f) a second plurality of calibration curves is obtained in the same way as the first series of calibration curves for a further wavelength range;
    (g) the thickness of said layer of said sample stack is determined from the intensity detected by said detector by means of said first and second series of calibration curves.

2. The method of claim 1, and wherein the intensity of the light reflected by a stack of layers is detected simultaneously for two wavelength ranges.

3. The method of claim 1, and wherein the wavelength ranges are selected such that in each wavelength range the influence of a thickness change of one layer on the intensity of the light reflected by the stack of layers is much larger than the influence of a thickness change of the other layers.

4. The method of claim 1, and wherein the wavelength ranges are selected such that the overall intensity of the reflected light is optimized.

5. The method of claim 1, and wherein the intensity of the reflected light is measured at more than two wavelength ranges.

6. The method of claim 1, and wherein the thickness of three or more layers of the stack is determined, by calibrating and detecting the intensity of the reflected light in three or more wavelength ranges.

7. The method of claim 1, and wherein the thickness of the layers of the reference stacks are determined by ellipsometry for calibration.

8. An assembly for determining the thickness of a layer in a sample stack of at least two layers comprising
    a light source for illuminating a stack of layers;
    a detector for detecting light reflected by the stack of layers in a defined first wavelength range, and
    two or more reference stacks of layers, where each layer of the reference stacks has a known thickness, the same material as the sample stack and the layers occur in the same order as in the sample stack;
    and wherein
    further reference stacks are provided, where the thickness of another, different layer is known for providing a first series of calibration curves in the first wavelength range;
    means for detecting light reflected by the stack of layers in a defined second wavelength range for providing a second series of calibration curves for a further wavelength range.

9. The assembly of claim 8, and wherein the light source is a light source with a continuous spectrum and one or more filters, an adjustable monochromator or another wavelength selection means is provided to define the measured wavelength range.

10. The assembly of claim 8, and wherein one or more light sources are provided which emit light in the defined wavelength ranges.

11. The assembly of claim 8, and wherein the different wavelength ranges are defined by two interference filters or a couple of interference filter pairs arranged in two filter wheels.

12. The assembly of claim 8, and wherein the different wavelength ranges are defined by a single or a combination of acusto-optical filters.

13. The assembly of claim 8, and wherein the detector is a line camera or an area camera.

\* \* \* \* \*